(12) United States Patent
Yonezawa

(10) Patent No.: US 12,115,323 B2
(45) Date of Patent: Oct. 15, 2024

(54) GUIDE WIRE

(71) Applicant: ASAHI INTECC CO., LTD., Seto (JP)

(72) Inventor: Satoshi Yonezawa, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 927 days.

(21) Appl. No.: 17/137,499

(22) Filed: Dec. 30, 2020

(65) Prior Publication Data

US 2021/0113818 A1    Apr. 22, 2021

Related U.S. Application Data

(63) Continuation of application No. PCT/JP2018/027066, filed on Jul. 19, 2018.

(51) Int. Cl.
*A61M 25/09*    (2006.01)

(52) U.S. Cl.
CPC ... *A61M 25/09* (2013.01); *A61M 2025/09091* (2013.01); *A61M 2025/09133* (2013.01); *A61M 2205/0216* (2013.01)

(58) Field of Classification Search
CPC ........ A61M 25/09; A61M 2025/09091; A61M 2025/09133; A61M 2205/0216
See application file for complete search history.

(56) References Cited

U.S. PATENT DOCUMENTS

| 4,953,553 A * | 9/1990 | Tremulis ............... A61B 5/0215 604/528 |
| 5,573,520 A * | 11/1996 | Schwartz .......... A61M 25/0013 604/526 |
| 6,001,068 A | 12/1999 | Uchino et al. |
| 6,602,208 B2 * | 8/2003 | Jafari ................ A61M 25/0905 600/585 |
| 2004/0039308 A1 | 2/2004 | Murayama et al. |
| 2008/0045908 A1 | 2/2008 | Gould et al. |
| 2008/0064989 A1 * | 3/2008 | Chen ..................... A61M 25/09 600/585 |
| 2008/0171217 A1 | 7/2008 | Mishima |

(Continued)

FOREIGN PATENT DOCUMENTS

| JP | H04-292174 A | 10/1992 |
| JP | H11-57014 A | 3/1999 |

(Continued)

OTHER PUBLICATIONS

U.S. Appl. No. 17/119,583, filed Dec. 11, 2020 in the name of Ushida et al.

(Continued)

*Primary Examiner* — Devin B Henson
*Assistant Examiner* — Jonathan M Haney
(74) *Attorney, Agent, or Firm* — Oliff PLC

(57) ABSTRACT

A guide wire includes a first core shaft, a second core shaft, a first tubular member, and a second tubular member. The first tubular member is disposed to cover (i) a contact portion where the first core shaft and the second core shaft are arranged opposite to each other so that their central axes coincide, and (ii) a part of each of the first core shaft and the second core shaft, the part being adjacent to the contact portion. The second tubular member, having a tubular shape, covers at least the first tubular member and is fixed to both the first core shaft and the second core shaft.

20 Claims, 12 Drawing Sheets

(56) References Cited

U.S. PATENT DOCUMENTS

| | | |
|---|---|---|
| 2008/0183182 A1 | 7/2008 | Satou et al. |
| 2008/0281396 A1 | 11/2008 | Shida et al. |
| 2011/0015618 A1 | 1/2011 | Satou et al. |
| 2011/0160703 A1 | 6/2011 | Matsumoto et al. |
| 2013/0046202 A1* | 2/2013 | Tsunezumi ............ A61M 25/09 600/585 |
| 2015/0005746 A1 | 1/2015 | Sato |
| 2016/0287842 A1 | 10/2016 | Sato |
| 2017/0072170 A1 | 3/2017 | Akitomo |

FOREIGN PATENT DOCUMENTS

| | | |
|---|---|---|
| JP | 2003-260140 A | 9/2003 |
| JP | 2004-016359 A | 1/2004 |
| JP | 2006-508739 A | 3/2006 |
| JP | 2006-511304 A | 4/2006 |
| JP | 2006-519069 A | 8/2006 |
| JP | 2007-503957 A | 3/2007 |
| JP | 2008-161589 A | 7/2008 |
| JP | 2008-188670 A | 8/2008 |
| JP | 4203358 B2 | 12/2008 |
| JP | 2010-240201 A | 10/2010 |
| JP | 2011-130976 A | 7/2011 |
| JP | 2013-544575 A | 12/2013 |
| JP | 2016-189998 A | 11/2016 |
| JP | 2017-080153 A | 5/2017 |
| JP | 2017-513604 A | 6/2017 |
| JP | 2017-521177 A | 8/2017 |
| WO | 95/19800 A2 | 7/1995 |
| WO | 1998/018516 A1 | 5/1998 |
| WO | 2004/050162 A1 | 6/2004 |
| WO | 2004/060462 A2 | 7/2004 |
| WO | 2004/075967 A1 | 9/2004 |
| WO | 2005/023357 A2 | 3/2005 |
| WO | 2008/139829 A1 | 11/2008 |
| WO | 2009/119386 A1 | 10/2009 |
| WO | 2012/058302 A1 | 5/2012 |
| WO | 2013/136581 A1 | 9/2013 |
| WO | 2015/164250 A1 | 10/2015 |
| WO | 2016/012902 A1 | 1/2016 |
| WO | 2016/047555 A1 | 3/2016 |
| WO | 2016/064753 A1 | 4/2016 |
| WO | 2016/167916 A1 | 10/2016 |

OTHER PUBLICATIONS

U.S. Appl. No. 17/150,019, filed Jan. 15, 2021 in the name of Yonezawa.

* cited by examiner

GUIDE WIRE

CROSS REFERENCE TO RELATED APPLICATION

This is a Continuation of PCT/JP2018/027066 filed Jul. 19, 2018. The disclosure of the prior application is hereby incorporated by reference herein in its entirety.

TECHNICAL FIELD

The disclosed embodiments relate to a guide wire.

BACKGROUND

There has been a known guide wire that is used for inserting a catheter or the like into a blood vessel. Such a guide wire requires flexibility and restorability against bending, torque transmissivity and pushability for transmitting an operation of the guide wire on a proximal portion to a distal end side, and strong kink resistance against deformation due to bending, wrinkling, and crushing. Incidentally, the torque transmissivity and the pushability are collectively referred to as "operability". For example, Patent Literatures 1 to 5 disclose that a guide wire is equipped with a first core shaft (first wire, insertion member) disposed on a distal end side, and a second core shaft (second wire, introduction member) disposed on a proximal end side of the first core shaft and joined to the first core shaft, so that the flexibility and the operability can be improved.

However, in the guide wire described in Patent Literature 1, each of a first core shaft and a second core shaft has notches, therefore it is difficult to coincide the central axes of the first and second core shafts, and there has been room for improvement in torque transmissivity (operability). In the guide wire described in Patent Literature 2, the first and second core shafts are joined by welding, therefore the first and second core shafts undergo deformation such as bending in the vicinity of the joint part in some cases, and there has been room for improvement in the kink resistance. In the guide wires described in Patent Literatures 3 to 5, although a joint part between the first and second core shafts is covered by an annular or tubular member (inner coil, tubular body, tubular joint member), there has still been room for improvement in the kink resistance. Incidentally, such problems are not limited to vascular systems, and are common to guide wires to be inserted into each organ in a human body, such as a lymphatic system, a biliary system, a urinary system, a respiratory system, a digestive system, a secretory gland, and a genital organ.

CITATION LIST

Patent Document 1: Japanese Patent Laid-Open No. 2004-16359
Patent Literature 2: Japanese Patent Publication No. 4203358
Patent Literature 3: PCT International Publication No. WO2013/136581, brochure
Patent Document 4: Japanese Patent Laid-Open No. 2008-188670
Patent Document 5: Japanese Patent Laid-Open No. 2003-260140

SUMMARY

The disclosed embodiments have been devised to address at least a part of the aforementioned problems, and an object of the disclosed embodiments is to provide a guide wire excellent in operability and kink resistance.

The disclosed embodiments include the following aspects.

(1) According to one aspect of the disclosed embodiments, a guide wire is provided. The guide wire includes: a first core shaft positioned on a distal end side; a second core shaft positioned on a proximal end side; a first tubular member disposed to cover (i) a contact portion, where the first core shaft and the second core shaft are arranged opposite to each other (end-to-end) to make central axes of the first core shaft and the second core shaft coincide with each other, and (ii) a part of each of the first core shaft and the second core shaft, the part being adjacent to the contact portion; and a second tubular member having a tubular shape, covering at least the first tubular member, and fixed to both the first core shaft and the second core shaft.

According to this configuration, since the first core shaft and the second core shaft face each other such that their central axes coincide with each other, an operation of the guide wire on a proximal portion can be transmitted to the distal end side, and torque transmissivity and pushability (operability) can be improved. In addition, since both (i) the contact portion between the first and second core shafts, and (ii) a part of each of the first and second core shafts adjacent to the contact portion are covered by the first tubular member, a rigidity gap between the first and second core shafts can be reduced by the first tubular member even if the first and second core shafts have different rigidities. Furthermore, since the guide wire includes the second tubular member covering the first tubular member and fixed to both the first and second core shafts, a rigidity gap among the first core shaft, the second core shaft, and the first tubular member can be reduced by the second tubular member even if they have different rigidities. Thereby, the deformation (bending, wrinkling, crushing) of the first and second core shafts in the vicinity of the contact portion, which has been conventionally caused, can be prevented, so that the kink resistance can be improved. As a result, this configuration makes it possible to provide a guide wire excellent in the operability and the kink resistance.

(2) In the guide wire according to the aforementioned aspect, the second tubular member has a length in an axial direction larger than the length in the axial direction of the first tubular member, and may cover at least a part of the first core shaft exposed from the first tubular member, and at least a part of the second core shaft exposed from the first tubular member. According to this configuration, since the second tubular member has the length in the axial direction larger than the length in the axial direction of the first tubular member and covers at least a part, exposed from the first tubular member, of each of the first and second core shafts, it is possible to prevent the deformation of the first and second core shafts in the vicinity of the contact portion, as well as the deformation of the first and second core shafts in the vicinity of the first tubular member, so that the kink resistance can be further improved.

(3) In the guide wire according to the aforementioned aspect, the second tubular member may be fixed together with the first core shaft, the second core shaft, and the first tubular member by a joining agent applied inside the second tubular member. According to this configuration, the second tubular member is fixed to the first and second core shafts and the first tubular member by the joining agent applied inside the second tubular member, so that the torque transmissivity (operability) and the kink resistance can be further improved.

(4) In the guide wire according to the aforementioned aspect, the first core shaft has a first large-diameter portion and a first small-diameter portion with a diameter smaller than that of the first large-diameter portion, and the second core shaft has a second large-diameter portion and a second small-diameter portion with a diameter smaller than that of the second large-diameter portion. The first tubular member covers (i) the contact portion, where an end portion of the first small-diameter portion and an end portion of the second small-diameter portion are arranged opposite to each other, and (ii) at least a part of each of the first small-diameter portion and the second small-diameter portion, the part being adjacent to the contact portion. The second tubular member may cover the first tubular member, and at least a part of each of the first large-diameter portion and the second large-diameter portion. According to this configuration, an effect of reducing the rigidity gap can be enhanced, and the kink resistance can be further improved by covering the contact portion and a part of each of the first and second small-diameter portions by the first tubular member, and by covering the first tubular member and a part of each of the first and second large-diameter portions by the second tubular member.

(5) In the guide wire according to the aforementioned aspect, the first tubular member is a multi-thread coil obtained by winding a plurality of wires, and the second tubular member may be made of a superelastic material. According to this configuration, the first tubular member disposed inside is formed into a multi-thread coil, and the second tubular member disposed outside is formed into a tubular shape made of a superelastic material, so that the effect of reducing the rigidity gap can be enhanced, and the kink resistance can be further improved.

(6) In the guide wire according to the aforementioned aspect, the first core shaft may be made of a superelastic material, and the second core shaft may be made of a material having a rigidity higher than of the first core shaft. According to this configuration, flexibility and restorability against bending can be improved by forming the first core shaft with a superelastic material, and the torque transmissivity and the pushability (operability) can be improved by forming the second core shaft with a material having a higher rigidity than of the first core shaft.

(7) In the guide wire according to the aforementioned aspect, the first tubular member is a tubular body made of a metal or a resin, and the tubular body may be made of a material having a rigidity lower than those of the first core shaft, the second core shaft, and the second tubular member. According to this configuration, in a structure in which a space between a contact portion of the first core shaft, the second core shaft and the second tubular member is filled with an adhesive or a solder agent, the integrated tubular body disperses a force applied to the contact portion in the longitudinal direction of the guide wire to spread the force to the first core shaft and the second core shaft. Thereby, a stress applied to the contact portion of the first core shaft and the second core shaft can be reduced, and the kink resistance can be further improved.

Incidentally, the disclosed embodiments can be achieved in various aspects, e.g. in a form of a core shaft product composed of a plurality of core shafts used in a guide wire, a method for manufacturing a guide wire, or the like.

DETAILED DESCRIPTION OF EMBODIMENTS

First Embodiment

Figure 1:
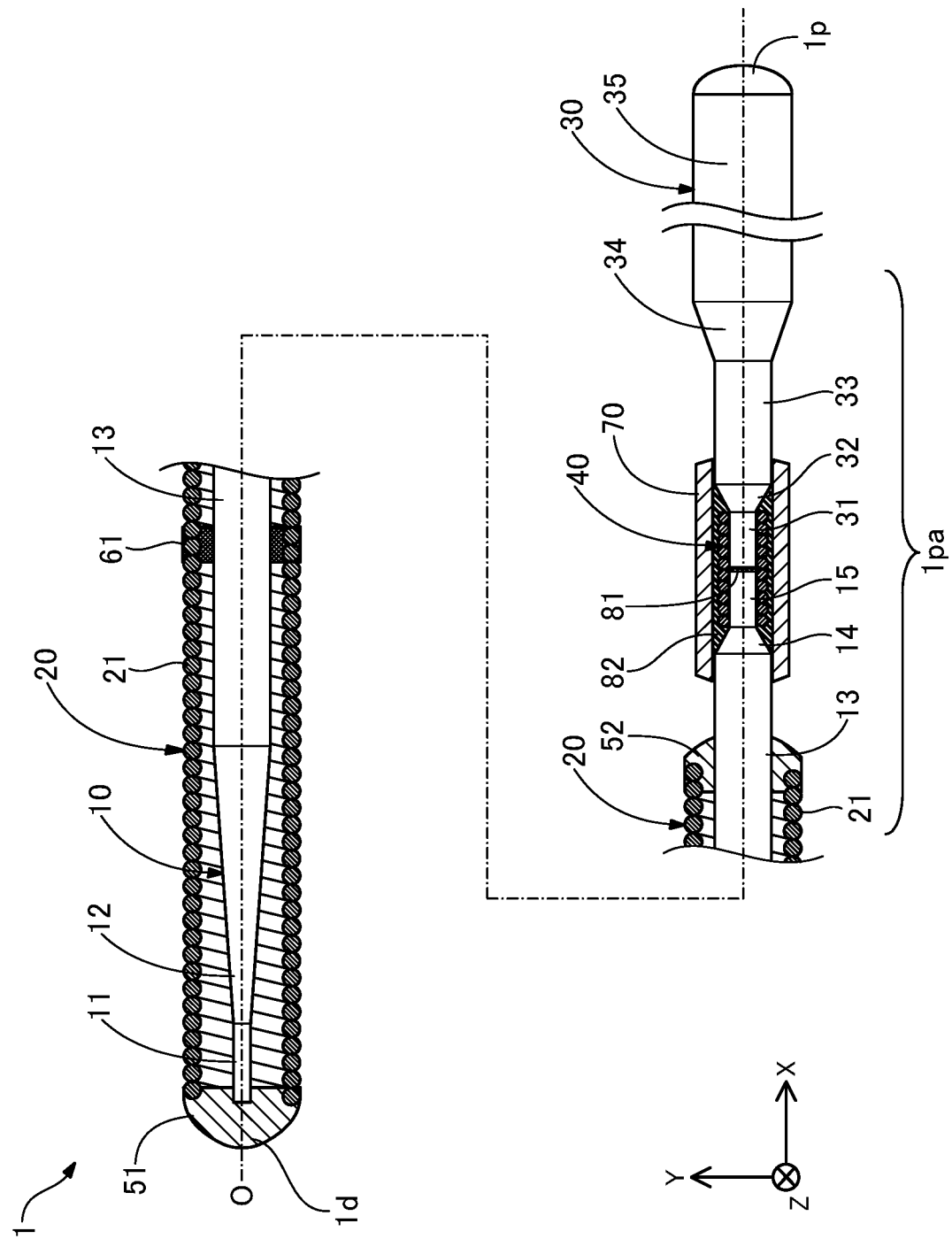
FIG. 1 is a partial sectional view illustrating an overall configuration of a guide wire according to the first embodiment.

FIG. 1 is a partial sectional view illustrating an overall configuration of a guide wire 1 according to the first embodiment. The guide wire 1 is e.g. a medical appliance used for inserting a catheter into a blood vessel, and includes a first core shaft 10, a coil body 20, a second core shaft 30, a coil body 40, a distal end-side fixation portion 51, a proximal end-side fixation portion 52, and an intermediate fixation portion 61, and a tubular member 70. In FIG. 1, an axis passing through a center of the guide wire 1 is represented by an axis line O (dot and dash line). In the following examples, all axes passing through a center of each member of the first core shaft 10, the coil body 20, the second core shaft 30, the coil body 40, and the tubular member 70 coincide with (are substantially the same as) the axis line O. However, each axis passing through the center of each of these members may be inconsistent with the axis line O. Incidentally, in the present embodiment, the coil body 40 corresponds to the "first tubular member", and the tubular member 70 corresponds to the "second tubular member".

In addition, XYZ axes that are orthogonal to each other are illustrated in FIG. 1. The X axis corresponds to the axial direction of the guide wire 1, the Y axis corresponds to a height direction of the guide wire 1, and the Z axis corresponds to a width direction of the guide wire 1. The left side (−X axis direction) of FIG. 1 is referred to as the "distal end side" of the guide wire 1 and each component, and the right side of FIG. 1 (+X axis direction) is referred to as the "proximal end side" of the guide wire 1 and each component. In addition, regarding the guide wire 1 and each component, the end portion positioned on the distal end side is referred to as the "distal end portion" or simply "distal end", and the end portion positioned on the proximal end side is referred to as the "proximal end portion" or simply "proximal end". In the present embodiment, the distal end side corresponds to the "farther side", and the proximal end side corresponds to the "nearer side". These regards are also common to the figures illustrating the overall configuration in FIG. 1 and the following figures.

The first core shaft 10 is a long member having a large diameter at the center and small diameters on both end sides (distal end side, proximal end side). The first core shaft 10 is made of a superelastic material e.g. an NiTi (nickel-titanium) alloy, or an alloy of NiTi and another metal. The first core shaft 10 has a distal small-diameter portion 11, a distal decreasing-diameter portion 12, a first large-diameter portion 13, a first intermediate portion 14, and a first small-diameter portion 15 in this order from the distal end side to the proximal end side. An outer diameter and a length of each portion can be arbitrarily determined.

The distal small-diameter portion 11 is disposed on the distal end portion of the first core shaft 10. The distal small-diameter portion 11 is a part where the outer diameter of the first core shaft 10 is smallest, and has a substantially cylindrical shape with a constant outer diameter. The distal decreasing-diameter portion 12 is disposed between the distal small-diameter portion 11 and the first large-diameter portion 13. The distal decreasing-diameter portion 12 has a substantially truncated cone shape with an outer diameter decreasing from the proximal end side to the distal end side. The first large-diameter portion 13 is disposed between the distal decreasing-diameter portion 12 and the first intermediate portion 14. The first large-diameter portion 13 is a part where the outer diameter of the first core shaft 10 is largest, and has a substantially cylindrical shape with a constant outer diameter. The first intermediate portion 14 is disposed between the first large-diameter portion 13 and the first small-diameter portion 15. The first intermediate portion 14 has a substantially truncated cone shape with an outer diameter increasing from the proximal end side to the distal end side. The first small-diameter portion 15 is disposed on the proximal end portion of the first core shaft 10. The first small-diameter portion 15 has a substantially cylindrical shape with a constant outer diameter smaller than that of the first large-diameter portion 13 and larger than that of the distal small-diameter portion 11.

The second core shaft 30 is a long, tapered member having a large diameter on the proximal end side and a small diameter on the distal end side. The second core shaft 30 is made of a material having a higher rigidity than the material of the first core shaft 10, e.g. a stainless steel alloy such as SUS304 and SUS316. The second core shaft 30 has a second small-diameter portion 31, a second intermediate portion 32, a second large-diameter portion 33, a proximal decreasing-diameter portion 34, and a proximal large-diameter portion 35 in this order from the distal end side to the proximal end side. An outer diameter and a length of each portion can be arbitrarily determined.

The second small-diameter portion 31 is disposed on the distal end portion of the second core shaft 30. The second small-diameter portion 31 is a part where the outer diameter of the second core shaft 30 is smallest, and has a substantially cylindrical shape with a constant outer diameter substantially equal to that of the first small-diameter portion 15 of the first core shaft 10. The second intermediate portion 32 is disposed between the second small-diameter portion 31 and the second large-diameter portion 33. The second intermediate portion 32 has a substantially truncated cone shape with an outer diameter decreasing from the proximal end side to the distal end side. The second large-diameter portion 33 is disposed between the second intermediate portion 32 and the proximal decreasing-diameter portion 34. The second large-diameter portion 33 has a substantially cylindrical shape with a constant outer diameter smaller than that of the proximal large-diameter portion 35 and larger than that of the second small-diameter portion 31. The proximal decreasing-diameter portion 34 is disposed between the second large-diameter portion 33 and the proximal large-diameter portion 35. The proximal decreasing-diameter portion 34 has a substantially truncated cone shape with an outer diameter decreasing from the proximal end side to the distal end side. The proximal large-diameter portion 35 is disposed on the proximal end portion of the second core shaft 30. The proximal large-diameter portion 35 is a part where the outer diameter of the second core shaft 30 is largest, and has a substantially cylindrical shape with a constant outer diameter.

In the first core shaft 10, the distal small-diameter portion 11, the distal decreasing-diameter portion 12, and the distal end side of the first large-diameter portion 13 are covered by the coil body 20 described later. On the other hand, in the first core shaft 10, the proximal end side of the first large-diameter portion 13 and each portion of the second core shaft 30 are not covered by the coil body 20 but are exposed from the coil body 20. The proximal large-diameter portion 35 of the second core shaft 30 is used when an operator grasps the guide wire 1.

The coil body 20 has a substantially hollow cylindrical shape formed by spirally winding a wire 21 around the first core shaft 10. The wire 21 constituting the coil body 20 may be a solid wire composed of one wire, or a twisted wire obtained by twisting a plurality of wires. When the wire 21 is a solid wire, the coil body 20 is configured as a single coil, and when the wire 21 is a twisted wire, the coil body 20 is configured as a hollow twisted wire coil. Alternatively, the coil body 20 may be configured by combining the single coil and the hollow twisted wire coil. The wire diameter of the wire 21 and an average coil diameter of the coil body 20 (average diameter of the outer diameter and the inner diameter of the coil body 20) can be arbitrarily determined.

The wire 21 can be made of e.g. a stainless steel alloy such as SUS304 and SUS316, a superelastic alloy such as an NiTi alloy, a piano wire, a radiolucent alloy such as nickel-chromium alloy and cobalt alloy, gold, platinum, tungsten, or a radiopaque alloy such as an alloy including the aforementioned elements (e.g. platinum-nickel alloy). Incidentally, the wire 21 may be made of a known material other than the aforementioned materials.

The distal end-side fixation portion 51 is disposed on the distal end portion of the guide wire 1 and integrally holds the distal end portion of the distal small-diameter portion 11 of the first core shaft 10, and the distal end portion of the coil body 20. The distal end-side fixation portion 51 can be formed from any joining agent, e.g. a metal solder such as silver solder, gold solder, zinc, Sn—Ag alloy, and Au—Sn alloy, or an adhesive such as epoxy adhesive. The proximal end-side fixation portion 52 is disposed on a part closer to the proximal end side of the first large-diameter portion 13 of the first core shaft 10 and integrally holds the first core shaft 10 and the proximal end portion of the coil body 20. The proximal end-side fixation portion 52 can be formed from any joining agent in the same manner as for the distal end-side fixation portion 51. For the proximal end-side fixation portion 52 and the distal end-side fixation portion 51, the same joining agent or different joining agents may be used.

The intermediate fixation portion 61 integrally holds the coil body 20 and the first core shaft 10 in the vicinity of the intermediate portion of the coil body 20 in the axis line O direction. The intermediate fixation portion 61 can be formed from any joining agent in the same manner as for the distal end-side fixation portion 51. For the intermediate fixation portion 61 and the distal end-side fixation portion 51, the same joining agent or different joining agents may be used. Although one intermediate fixation portion 61 has been described as an example in FIG. 1, a plurality of intermediate fixation portions 61 may be disposed on the guide wire 1.

Figure 2:
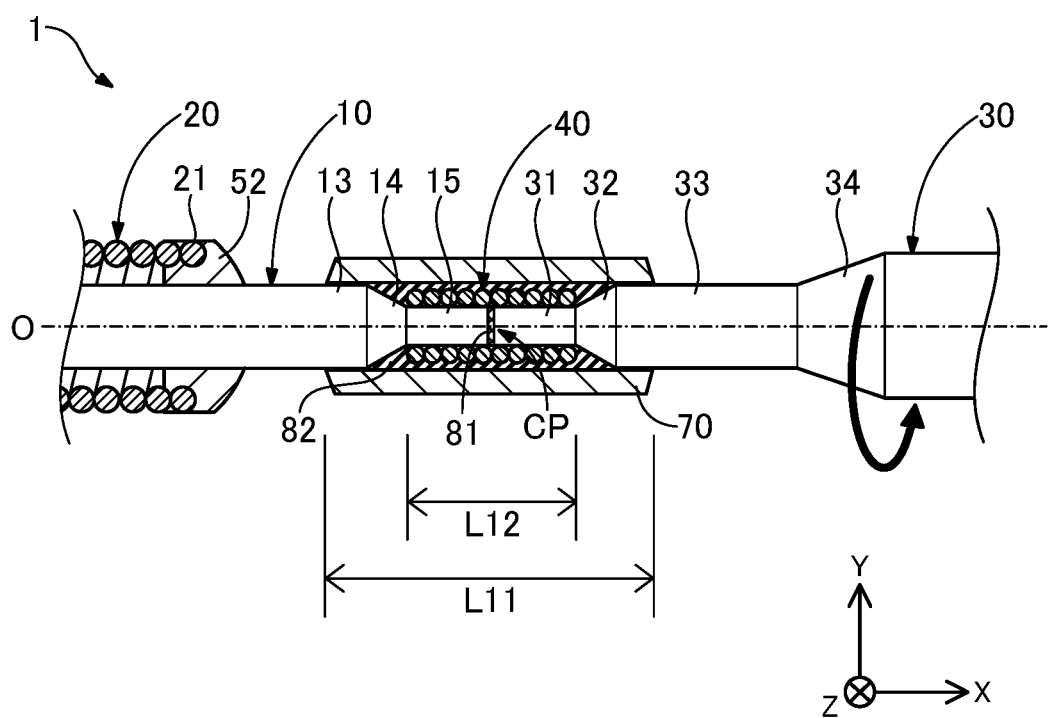
FIG. 2 is a partial sectional view illustrating a vicinity of a contact portion between first and second core shafts (FIG. 1).

FIG. 2 is a partial sectional view illustrating a vicinity 1pa of a contact portion between the first and second core shafts 10 and 30 (FIG. 1). XYZ axes illustrated in FIG. 2 correspond to the XYZ axes respectively in FIG. 1. The same applies to the figures with XYZ axes in FIG. 2 and the following figures. The first and second core shafts 10 and 30 face each other such that their central axes coincide with each other. In the example of the figure, each central axis of the first and second core shafts 10 and 30 coincides with the axis line O. However, the central axes of the first and second core shafts 10 and 30 may coincide with each other at a position on a YZ plane different from the axis line O. Hereinafter, a part where the first and second core shafts 10 and 30 face each other will be referred to as "contact portion CP". In the example of the figure, the contact portion CP is a part where the proximal end portion of the first small-diameter portion 15 in the first core shaft 10 and the distal end portion of the second small-diameter portion 31 in the second core shaft 30 are adjacent to each other.

In the present embodiment, the first and second core shafts 10 and 30 are joined to each other on the contact portion CP. The joining can be performed e.g. in such a way that a gap between the first small-diameter portion 15 of the first core shaft 10 and the second small-diameter portion 31 of the second core shaft 30 adjacent to each other on the contact portion CP is filled with a joining agent 81 and the joining agent 81 is hardened. In this case, the joining agent 81 may be applied on the whole gap between the first small-diameter portion 15 and the second small-diameter portion 31 (in other words, the whole face between the end face on the proximal end side of the first small-diameter portion 15 and the end face on the distal end side of the second small-diameter portion 31), and alternatively the joining agent 81 may be applied only on a part of the gap and the other part may be a void. As the joining agent 81, e.g. a metal solder such as silver solder, gold solder, zinc, Sn—Ag alloy, and Au—Sn alloy, or an adhesive such as epoxy adhesive can be used. In addition, joining on the contact portion CP may be performed by welding the first and second core shafts 10 and 30.

Incidentally, the first and second core shafts 10 and 30 are not necessarily joined to each other on the contact portion CP. In this case, on the contact portion CP, the end face on the proximal end side of the first small-diameter portion 15 and the end face on the distal end side of the second small-diameter portion 31 may be in contact with each other, or alternatively the end face on the proximal end side of the first small-diameter portion 15 and the end face on the distal end side of the second small-diameter portion 31 may be adjacent to each other via a void therebetween.

Figure 3:
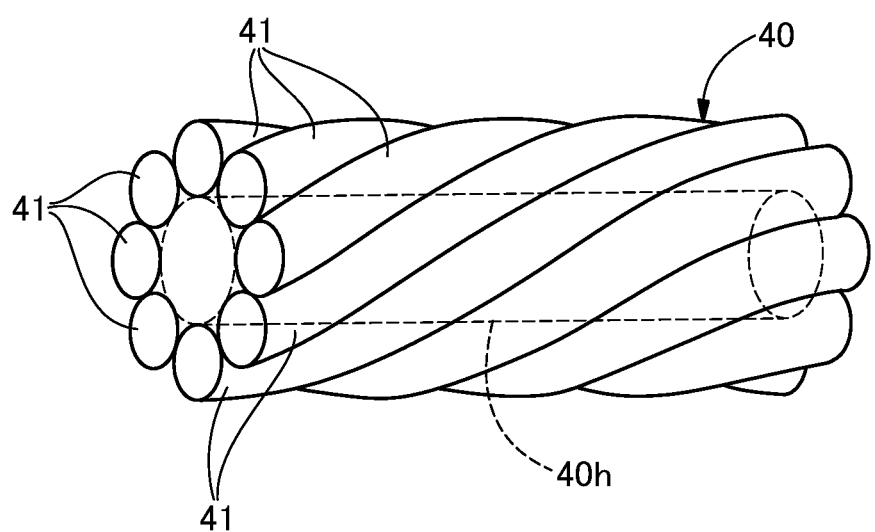
FIG. 3 is a perspective view illustrating a schematic configuration of a coil body.

FIG. 3 is a perspective view illustrating a schematic configuration of the coil body 40. The coil body 40 according to the present embodiment is a multi-thread coil obtained by winding eight wires 41, and has a substantially hollow cylindrical shape with a constant outer diameter. The coil body 40 is preferably configured to have a lower bending rigidity than the second core shaft 30. The coil body 40 can be formed e.g. in such a way that the eight wires 41 are tightly twisted around a cored bar so as to be in contact with each other, then a residual stress is removed using a known heat treatment method, and the cored bar is drawn out. The coil body 40 formed in this way is a multi-thread coil having an inner cavity 40h (FIG. 3: dashed line) as illustrated in FIG. 3. A material of the wire 41 may or may not be the same as that of the wire 21. Incidentally, for the coil body 40, any aspect can be adopted. For example, the number of wires constituting the coil body 40 is not limited to eight, and can be arbitrarily determined. The coil body 40 is not limited to the multi-thread coil, and may be a single-thread coil formed from one wire, or alternatively may be coated with a hydrophobic resin material, a hydrophilic resin material, or a mixture thereof.

As illustrated in FIG. 2, the coil body 40 is disposed so as to cover the contact portion CP between the first and second core shafts 10 and 30, a part of the first core shaft 10 adjacent to the contact portion CP (in the example of the figure, the first small-diameter portion 15), and a part of the second core shaft 30 adjacent to the contact portion CP (in the example of the figure, the second small-diameter portion 31). In other words, the first and second core shafts 10 and 30 joined to each other on the contact portion CP extend in the axis line O direction passing through the inner cavity 40h of the coil body 40. In the present embodiment, a length L12 of the coil body 40 in the axis line O direction is substantially equal to a sum of the length of the first small-diameter portion 15 in the axis line O direction and the length of the second small-diameter portion 31 in the axis line O direction. Incidentally, the length L12 of the coil body 40 can be arbitrarily determined.

The tubular member 70 according to the present embodiment is a metal member formed into a tubular shape (substantially hollow cylindrical shape) having a constant outer diameter. The tubular member 70 is preferably configured to have a lower bending rigidity than the second core shaft 30 and to have an elastic modulus equivalent to that of the first core shaft 10. Similar to the first core shaft 10, the tubular member 70 can be made of a superelastic material, e.g. an NiTi alloy, or an alloy of NiTi and another metal. The tubular member 70 may be made of the same or a different material as or from that of the first core shaft 10.

As illustrated in FIG. 2, the tubular member 70 is disposed so as to cover the coil body 40, a part of the first core shaft 10 exposed from the coil body 40 (in the example of the figure, the first intermediate portion 14 and a part on the proximal end side of the first large-diameter portion 13), and a part of the second core shaft 30 exposed from the coil body 40 (in the example of the figure, the second intermediate portion 32, and a part on the distal end side of the second large-diameter portion 33). In other words, the first and second core shafts 10 and 30 covered by the coil body 40 extend in the axis line O direction to pass through an inner cavity of the tubular member 70. In the present embodiment, a length L11 of the tubular member 70 in the axis line O direction is larger than a length L12 of the coil body 40 in the axis line O direction. Incidentally, the length L11 of the tubular member 70 can be arbitrarily determined.

In addition, the tubular member 70 is fixed together with the first and second core shafts 10 and 30 and the coil body 40 by a joining agent 82 applied inside the tubular member 70. The tubular member 70 is fixed by filling the gap between the tubular member 70 and each member (first core shaft 10, second core shaft 30, coil body 40) covered by the tubular member 70, with the joining agent 82, and by hardening the joining agent 82. In this case, as illustrated in the figure, the joining agent 82 may be applied to the whole or only a part of the gap between the tubular member 70 and each member. When the joining agent 82 is applied to only a part, a void may remain between the tubular member 70 and each member covered by the tubular member 70. In addition, the joining agent 82 is applied to between each wire 41 of the coil body 40 to fix the coil body 40. Furthermore, the coil body 40 may be fixed together with the first and second core shafts 10 and 30 by applying the joining agent 82 also to the inside of the coil body 40. As the joining agent 82, any joining agent can be used, similarly to the joining agent 81. For the joining agent 82 and the joining agent 81, the same joining agent or different joining agents may be used.

As described above, in the guide wire 1 according to the present embodiment, the first core shaft 10 and the second core shaft 30 face each other such that their central axes coincide with each other. Thus, an operation of the guide wire 1 on the proximal portion, such as an operation of grasping and turning the proximal large-diameter portion 35 of the first core shaft 10 (FIG. 2: bold arrow) and an operation of pushing the proximal large-diameter portion 35 of the second core shaft 30, can be transmitted to the distal end side of the guide wire 1 (first core shaft 10), and torque transmissivity and pushability (operability) of the guide wire 1 can be improved.

In addition, the contact portion CP between the first and second core shafts 10 and 30, and a part of each of the first and second core shafts 10 and 30 adjacent to the contact portion CP are covered by the coil body 40. Thus, the rigidity gap between the first and second core shafts 10 and 30 (resulting from the different materials used for the first and second core shafts 10 and 30, or the like) can be reduced by the coil body 40 even if the first and second core shafts 10 and 30 have different rigidities. Herein, when the bending rigidity of the coil body 40 is made lower than that of the second core shaft 30, the effect of reducing the rigidity gap by the coil body 40 can be enhanced. Furthermore, the guide wire 1 includes the tubular member 70 covering the coil body 40 and fixed to both the first and second core shafts 10 and 30. Thus, even if the first core shaft 10, the second core shaft 30, and the coil body 40 have different rigidities, the rigidity gap among them can be reduced by the tubular member 70. Herein, when the bending rigidity of the tubular member 70 is made lower than that of the second core shaft 30 and the elastic modulus of the tubular member 70 is made equivalent to that of the first core shaft 10, the effect of reducing the rigidity gap by the guide wire 70 can be enhanced. Thereby, in the guide wire 1 according to the present embodiment, deformation (bending wrinkling, crushing) of the first and second core shafts 10 and 30 in the vicinity of the contact portion CP, which has been conventionally caused, can be prevented, so that kink resistance of the guide wire 1 can be improved.

Furthermore, the contact portion CP is covered by the coil body 40, and the coil body 40 is covered by the tubular member 70 fixed to the first and second core shafts 10 and 30, so that lateral dislocation of the first and second core shafts 10 and 30 during the operation can be prevented, and concentration of shear stress can be prevented. As a result, according to this configuration, the guide wire 1 excellent in the operability and the kink resistance can be provided.

Furthermore, in the guide wire 1 according to the present embodiment, the tubular member 70 has the length L11 in the axis line O direction that is larger than the length L12 of the coil body 40 in the axis line O direction (FIG. 2) and covers at least a part, exposed from the coil body 40, of each of the first and second core shafts 10 and 30. Thus, not only deformation of the first and second core shafts 10 and 30 in the vicinity of the contact portion CP but also deformation of the first and second core shafts 10 and 30 in the vicinity of the coil body 40 can be prevented, so that the kink resistance can be further improved. Furthermore, the tubular member 70 is fixed to the first and second core shafts 10 and 30 and the coil body 40 by the joining agent 82 applied inside the tubular member 70. Thereby, the operability (especially torque transmissivity) and the kink resistance can be further improved.

Furthermore, in the guide wire 1 according to the present embodiment, the coil body 40 covers the contact portion CP and the first and second small-diameter portions 15 and 31 of the first and second core shafts 10 and 30, and the tubular member 70 covers the coil body 40 and a part of the first and second large-diameter portions 13 and 33 of the first and second core shafts 10 and 30, so that the effect of reducing the rigidity gap by the coil body 40 and the tubular member 70 can be enhanced, and the kink resistance can be further improved.

Furthermore, in the guide wire 1 according to the present embodiment, the coil body 40 is formed into a multi-thread coil (FIG. 3), and the tubular member 70 disposed outside the coil body 40 is formed into a tube shape made of a superelastic material, the effect of reducing the rigidity gap can be enhanced, and the kink resistance can be further improved. Furthermore, the first core shaft 10 is made of a superelastic material, so that the flexibility and restorability against bending can be improved. The second core shaft 30 is made of a material having a higher rigidity than that of the first core shaft 10, so that the torque transmissivity and the pushability (operability) can be improved.

Furthermore, in the guide wire 1 according to the present embodiment, if the coil body 40 has a lower rigidity than the rigidities of each of the first core shaft 10, the second core shaft 30, and the tubular member 70, the coil body 40 disperses the force applied to the contact portion CP toward the axis line O direction (longitudinal direction) of the guide wire 1 to facilitate spreading of the force to the first and second core shafts 10 and 30, in a structure in which the space between the first and second core shafts 10 and 30 including the contact portion CP and the tubular member 70 is filled with the joining agent (adhesive or solder agent). Thereby, a stress applied to the contact portion CP between the first and second core shafts 10 and 30 can be further reduced, and the kink resistance can be further improved.

Second Embodiment

Figure 4:
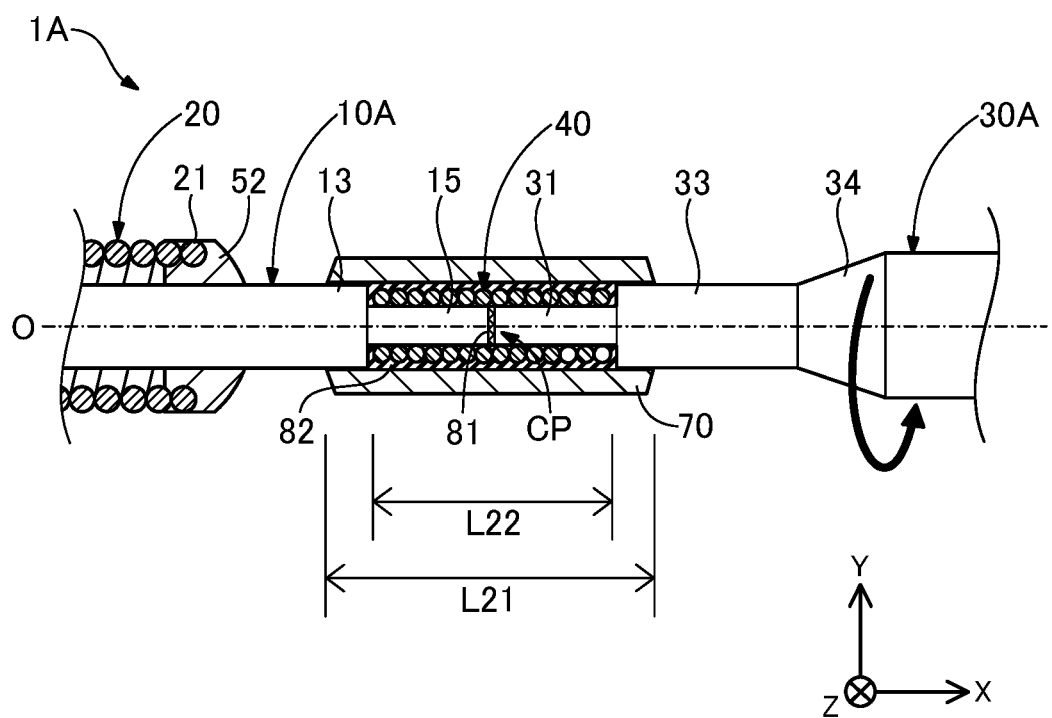
FIG. 4 is a partial sectional view illustrating a vicinity of a contact portion between first and second core shafts of a guide wire according to the second embodiment.

FIG. 4 is a partial sectional view illustrating a vicinity of a contact portion between first and second core shafts 10A and 30A in a guide wire 1A according to the second embodiment. In the guide wire 1A according to the second embodiment, the first core shaft 10A does not include the first intermediate portion 14, and the second core shaft 30A does not include the second intermediate portion 32 in the configuration according to the first embodiment. Also, in the second embodiment, a length L21 of the tubular member 70 in the axis line O direction is larger than a length L22 of the coil body 40 in the axis line O direction. The lengths L21 and L22 can be arbitrarily determined.

In this way, the proximal end side of the first core shaft 10A may be composed of the first large-diameter portion 13 and the first small-diameter portion 15, and the distal end side of the second core shaft 30A may be composed of the second large-diameter portion 33 and the second small-diameter portion 31. Incidentally, at least one of the first and second core shafts 10A and 30A may be configured according to the second embodiment and the other may be configured according to the first embodiment. The same effect as in the first embodiment can also be exhibited by the guide wire 1A according to the second embodiment.

Third Embodiment

Figure 5:
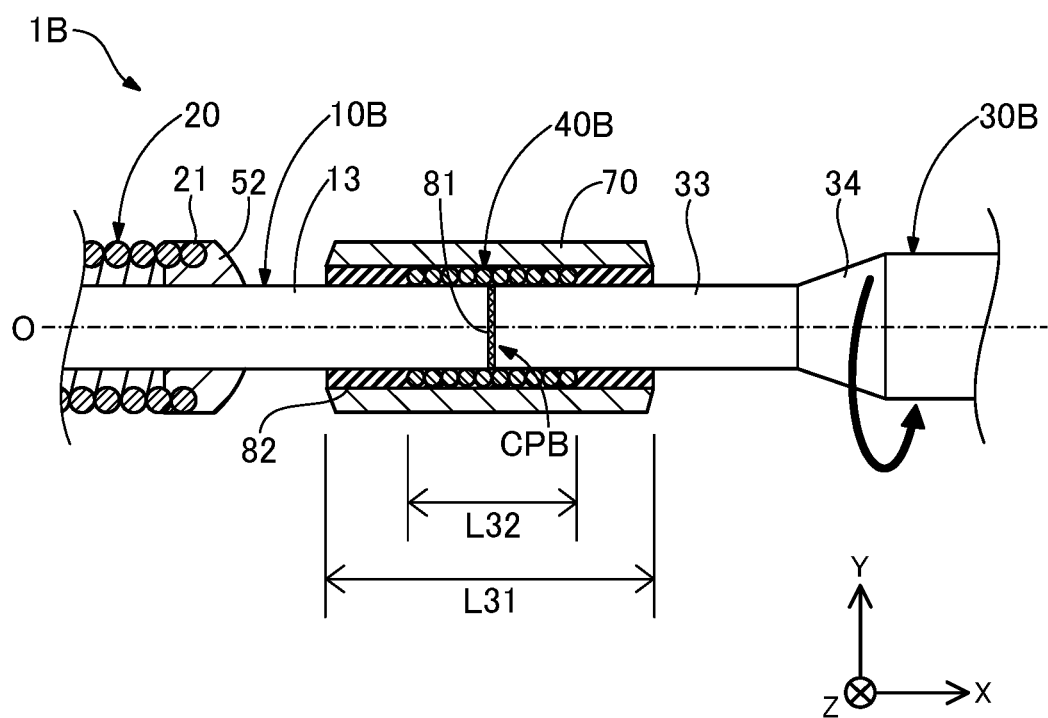
FIG. 5 is a partial sectional view illustrating a vicinity of a contact portion between first and second core shafts of a guide wire according to the third embodiment.

FIG. 5 is a partial sectional view illustrating a vicinity of a contact portion between first and second core shafts 10B and 30B of a guide wire 1B according to the third embodiment. In the guide wire 1B according to the third embodiment, the first core shaft 10B does not include the first intermediate portion 14 and the first small-diameter portion 15, and the second core shaft 30B does not include the second small-diameter portion 31 and the second intermediate portion 32 in the configuration according to the first embodiment. In the third embodiment, a contact portion CPB is an adjacent portion between the proximal end portion of the first large-diameter portion 13 in the first core shaft 10B and the distal end portion of the second large-diameter portion 33 in the second core shaft 30B. A coil body 40B covers the contact portion CPB, a part of the first core shaft 10B adjacent to the contact portion CPB (in the example of the figure, a part on the distal end side of the proximal end portion of the first large-diameter portion 13), and a part of the second core shaft 30B adjacent to the contact portion CPB (in the example of the figure, a part on the proximal end side of the distal end portion of the second large-diameter portion 33). Also, in the third embodiment, a length L31 of the tubular member 70 in the axis line O direction is larger than a length L32 of the coil body 40B in the axis line O direction. The lengths L31 and L32 can be arbitrarily determined.

In this way, the proximal end side of the first core shaft 10B may be composed only of the first large-diameter portion 13, and the distal end side of the second core shaft 30B may be composed only of the second large-diameter portion 33. Incidentally, at least one of the first and second core shafts 10B and 30B may be configured according to the third embodiment and the other may be configured according to the second or first embodiment. The same effect as in the first embodiment can also be exhibited by guide wire 1B according to the third embodiment.

Fourth Embodiment

Figure 6:
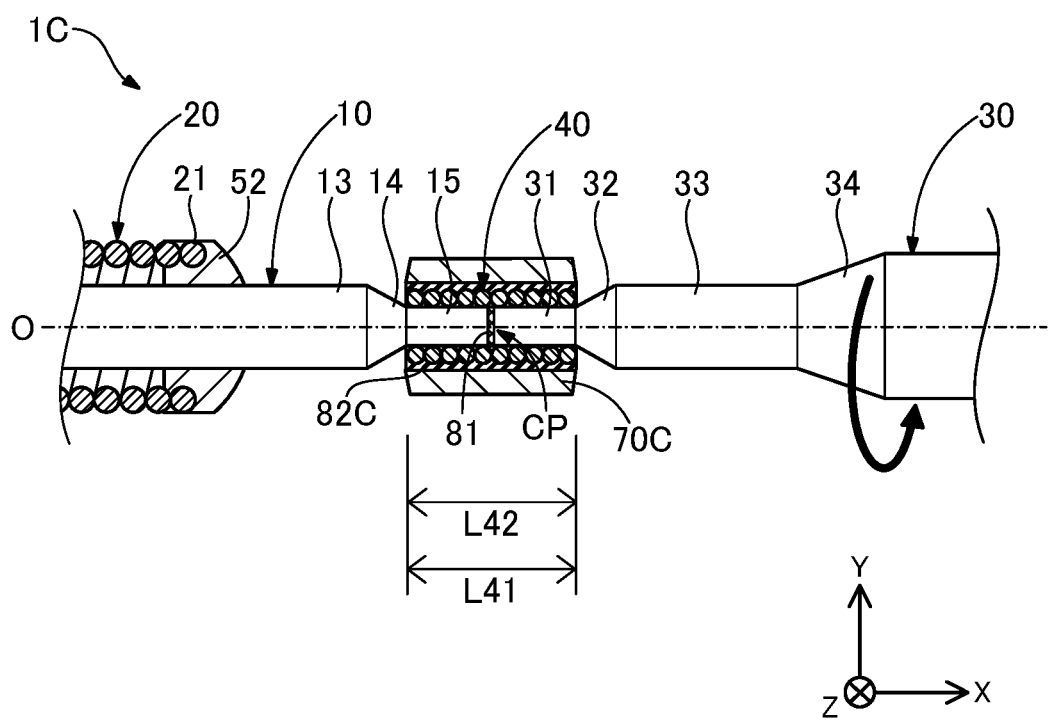
FIG. 6 is a partial sectional view illustrating a vicinity of a contact portion between first and second core shafts of a guide wire according to the fourth embodiment.

FIG. 6 is a partial sectional view illustrating a vicinity of a contact portion between first and second core shafts 10 and 30 of a guide wire 1C according to the fourth embodiment. The guide wire 1C according to the fourth embodiment includes a tubular member 70C of which a length L41 in the axis line O direction is substantially equal to a length L42 of the coil body 40 in the axis line O direction in the configuration according to the first embodiment. The tubular member 70C is fixed together with the first and second core shafts 10 and 30 and the coil body 40 by a joining agent 82C applied inside the tubular member 70C. For example, when the joining agent 82C is applied only to the gap between the tubular member 70C and the coil body 40, the tubular member 70C is indirectly fixed to the first and second core shafts 10 and 30 via the coil body 40. On the other hand, for example, it is preferable that the joining agent 82C is applied to the gap between the tubular member 70C and the coil body 40 and additionally to the gap between the coil body 40 and the first and second core shafts 10 and 30 (first small-diameter portion 15, second small-diameter portion 31), because the tubular member 70C is directly fixed to the first and second core shafts 10 and 30.

In this way, the length L41 of the tubular member 70C in the axis line O direction and the length L42 of the coil body 40 in the axis line O direction can be arbitrarily determined. For example, the lengths L41 and L42 may be substantially equal as described above, or the length L41 of the tubular member 70C in the axis line O direction may be smaller than the length L42 of the coil body 40 in the axis line O direction. Also in this guide wire 1C according to the fourth embodiment, operability of the guide wire 1C can be improved by the first and second core shafts 10 and 30 facing each other such that their central axes coincide with each other, in the same manner as in the first embodiment. In addition, deformation (bending, wrinkling, crushing) of the first and second core shafts 10 and 30 in the vicinity of the contact portion CP can be prevented by the coil body 40 and the tubular member 70C, so that kink resistance of the guide wire 1C can be improved.

Fifth Embodiment

Figure 7:
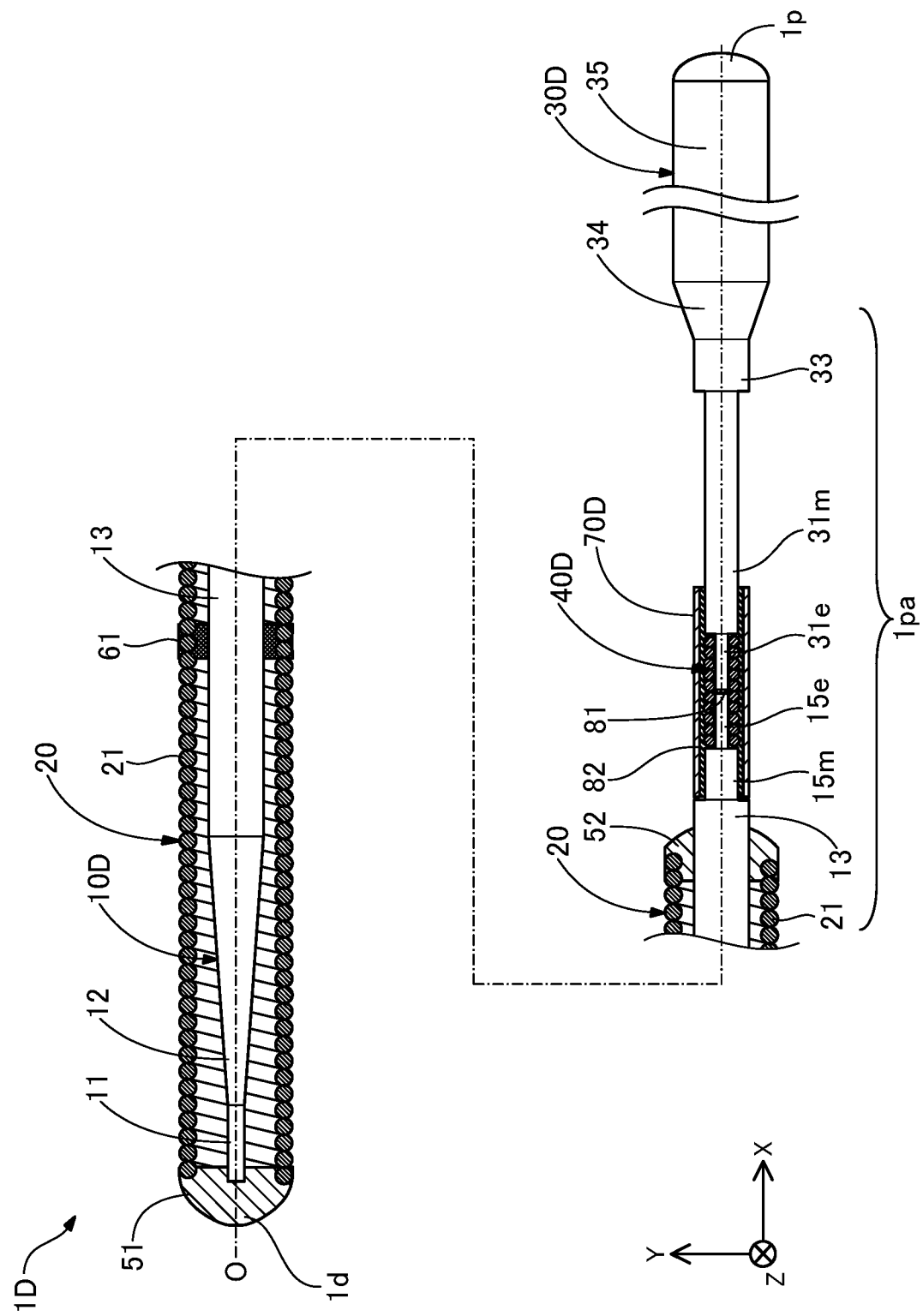
FIG. 7 is a partial sectional view illustrating an overall configuration of a guide wire according to the fifth embodiment.
Figure 8:
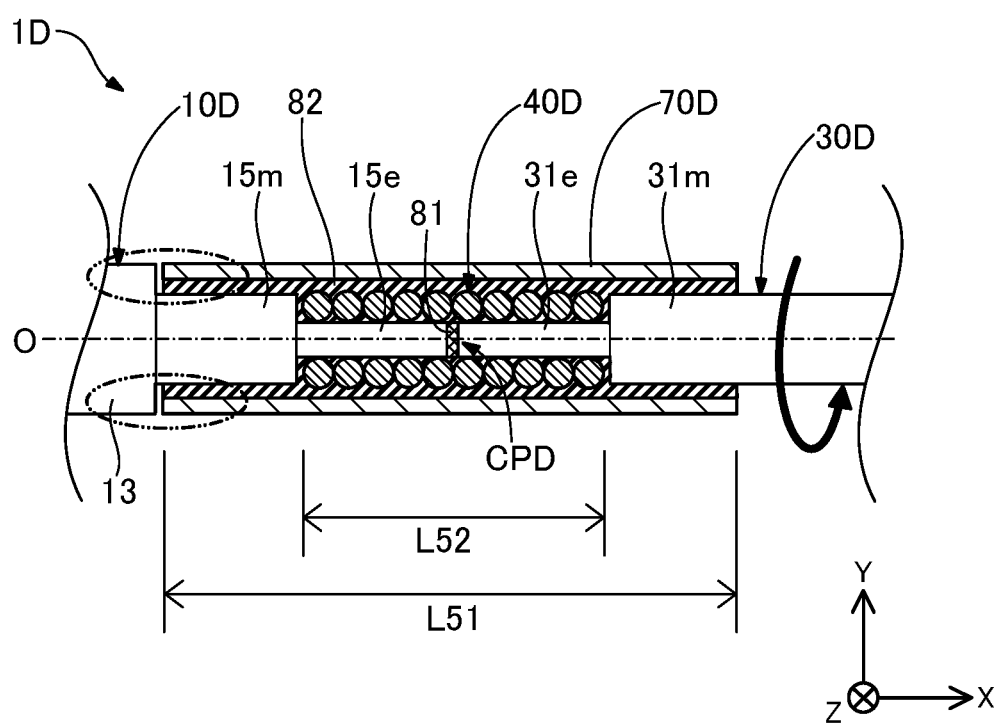
FIG. 8 is a partial sectional view illustrating a vicinity of a contact portion between first and second core shafts of the guide wire according to the fifth embodiment (FIG. 7).

FIG. 7 is a partial sectional view illustrating an overall configuration of a guide wire 1D according to the fifth embodiment. FIG. 8 is a partial sectional view illustrating a vicinity 1pa of a contact portion between first and second core shafts 10D and 30D of the guide wire 1D according to the fifth embodiment (FIG. 7). In the guide wire 1D according to the fifth embodiment, configurations of the first and second core shafts 10D and 30D, a coil body 40D, and a tubular member 70D in the vicinity 1pa of the contact portion is different from those in the first embodiment.

Specifically, the first core shaft 10D does not include the first intermediate portion 14, and the first small-diameter portion 15 includes a first end portion-side small-diameter portion 15e and a first intermediate small-diameter portion 15m. The first end portion-side small-diameter portion 15e is disposed on a proximal end portion side of the first core shaft 10D and has a substantially cylindrical shape with a constant outer diameter smaller than that of the first intermediate small-diameter portion 15m. The first intermediate small-diameter portion 15m is disposed between the first end portion-side small-diameter portion 15e and the first large-diameter portion 13 and has a substantially cylindrical shape with a constant outer diameter larger than that of the first end portion-side small-diameter portion 15e and smaller than that of the first large-diameter portion 13. The second core shaft 30D does not include the second intermediate portion 32, and the second small-diameter portion 31 includes a second end portion-side small-diameter portion 31e and a second intermediate small-diameter portion 31m. The second end portion-side small-diameter portion 31e is disposed on the distal end portion side of the second core shaft 30D and has a substantially cylindrical shape with a constant outer diameter smaller than that of the second intermediate small-diameter portion 31m. The second intermediate small-diameter portion 31m is disposed between the second end portion-side small-diameter portion 31e and the second large-diameter portion 33 and has a substantially cylindrical shape with a constant outer diameter larger than that of the second end portion-side small-diameter portion 31e and smaller than that of the second large-diameter portion 33.

As illustrated in FIG. 8, in a contact portion CPD, an end face on the proximal end side of the first end portion-side small-diameter portion 15e in the first core shaft 10D and an end face on the distal end side of the second end portion-side small-diameter portion 31e in the second core shaft 30D are adjacent to each other. On the contact portion CPD, the first and second core shafts 10D and 30D are joined to each other. For this joining, various aspects can be adopted, and joining may be omitted, in the same manner as in the first embodiment.

The coil body 40D is disposed so as to cover the contact portion CPD, a part of the first core shaft 10D adjacent to the contact portion CPD (in the example of the figure, the first end portion-side small-diameter portion 15e), and a part of the second core shaft 30D adjacent to the contact portion CPD (in the example of the figure, the second end portion-side small-diameter portion 31e). In the present embodiment, a length L52 of the coil body 40D in the axis line O direction is substantially equal to a sum of the length of the first end portion-side small-diameter portion 15e in the axis line O direction and the length of the second end portion-side small-diameter portion 31e in the axis line O direction. Incidentally, the length L52 of the coil body 40D can be arbitrarily determined.

The tubular member 70D is disposed so as to cover the coil body 40D, a part of the first core shaft 10D exposed from the coil body 40D (in the example of the figure, the first intermediate small-diameter portion 15m of the first small-diameter portion 15), and a part of the second core shaft 30D exposed from the coil body 40D (in the example of the figure, a part on the distal end side of the second intermediate small-diameter portion 31m of the second small-diameter portion 31). In the present embodiment, a length L51 of the tubular member 70D in the axis line O direction is substantially equal to a sum of the length of the first intermediate small-diameter portion 15m in the axis line O direction and the length of the second intermediate small-diameter portion 31m in the axis line O direction. In addition, the length L51 of the tubular member 70D in the axis line O direction is larger than the length L52 of the coil body 40D in the axis line O direction. Incidentally, the length L51 of the tubular member 70D can be arbitrarily determined.

In addition, the tubular member 70D according to the present embodiment is disposed such that its distal end portion is positioned in a vicinity of a boundary between the first large-diameter portion 13 and the first small-diameter portion 15 (first intermediate small-diameter portion 15m) of the first core shaft 10D. In this arrangement, as illustrated in FIG. 8, when the outer diameters of the tubular member 70D and the first large-diameter portion 13 are substantially equal, a connection portion (FIG. 8: two-dot and dash line) between the first core shaft 10D and the tubular member 70D can be formed into a flat shape without unevenness, so that a less invasive guide wire 1D can be provided. Incidentally, the tubular member 70D may be disposed such that its proximal end portion is positioned in a vicinity of a boundary between the second large-diameter portion 33 and the second small-diameter portion 31 (second intermediate small-diameter portion 31m) of the second core shaft 30D. In addition, the tubular member 70D may be disposed at a distance from the aforementioned boundary portion of the first core shaft 10D and the aforementioned boundary portion of the second core shaft 30D.

In this way, the first small-diameter portion 15 of the first core shaft 10D may be composed of a plurality of small-diameter portions (first intermediate small-diameter portion 15m, first end portion-side small-diameter portion 15e) having different configurations, and the second small-diameter portion 31 of the second core shaft 30D may be composed of a plurality of small-diameter portions (second intermediate small-diameter portion 31m, second end portion-side small-diameter portion 31e) having different configurations. Incidentally, at least one of the first and second core shafts 10D and 30D may be configured according to the fifth embodiment, and the other may be configured according to the first embodiment. The same effect as in the first embodiment can also be exhibited by the guide wire 1D according to the fifth embodiment.

Sixth Embodiment

Figure 9:
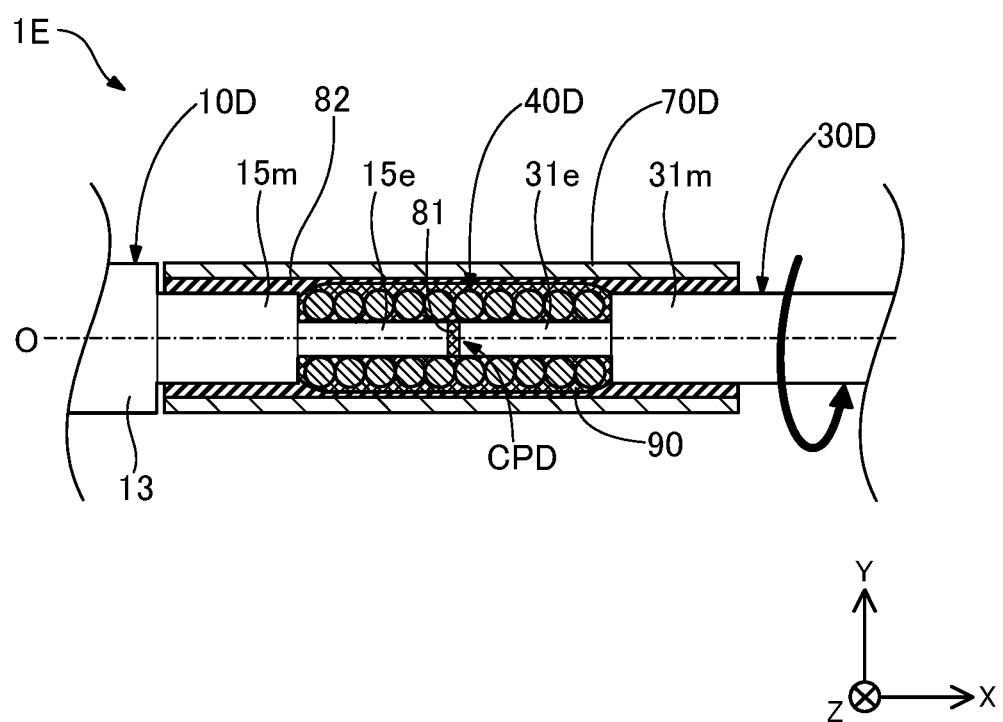
FIG. 9 is a partial sectional view illustrating a vicinity of a contact portion between first and second core shafts of a guide wire according to the sixth embodiment.

FIG. 9 is a partial sectional view illustrating a vicinity of a contact portion between first and second core shafts 10D and 30D of a guide wire 1E according to the sixth embodiment. The guide wire 1E according to the sixth embodiment includes an inner fixation portion 90 for fixing the coil body 40D to the first and second core shafts 10D and 30D in the configuration according to the fifth embodiment. The inner fixation portion 90 is disposed so as to cover the coil body 40D, and integrally fixes the first end portion-side small-diameter portion 15e of the first core shaft 10D, the second end portion-side small-diameter portion 31e of the second core shaft 30D, and the coil body 40D. The inner fixation portion 90 can be formed from any joining agent, similarly to the joining agent 81 and the joining agent 82. For the inner fixation portion 90 and the joining agents 81 and 82, the same joining agent or different joining agents may be used.

In this way, the coil body 40D and the tubular member 70D may be individually fixed to the first and second core shafts 10D and 30D respectively. The same effect as in the first embodiment can also be exhibited by the guide wire 1E according to the sixth embodiment. Additionally, in manufacturing the guide wire 1E, the guide wire 1E according to the sixth embodiment makes it possible to individually perform the step of fixing the coil body 40D (forming the inner fixation portion 90) to the first and second core shafts 10D and 30D and the step of fixing the tubular member 70D (applying the joining agent 82) to the first and second core shafts 10D and 30D.

Seventh Embodiment

Figure 10:
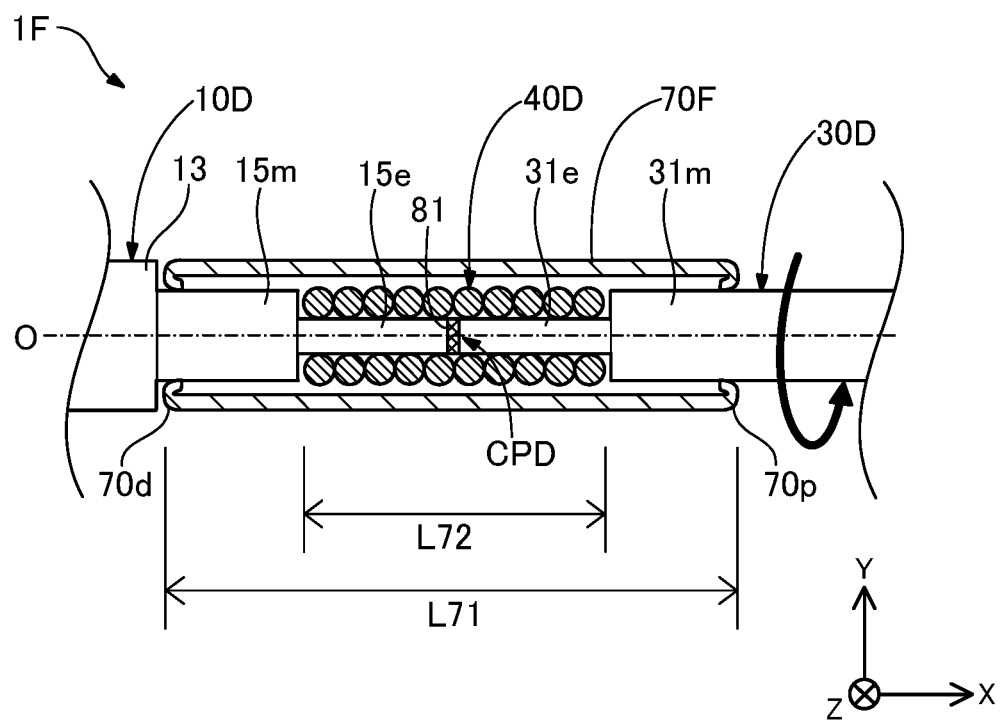
FIG. 10 is a partial sectional view illustrating a vicinity of a contact portion between first and second core shafts of a guide wire according to the seventh embodiment.

FIG. 10 is a partial sectional view illustrating a vicinity of a contact portion between first and second core shafts 10D and 30D of a guide wire 1F according to the seventh embodiment. The guide wire 1F according to the seventh embodiment includes a tubular member 70F fixed to the first and second core shafts 10D and 30D using no joining agent in the configuration according to the fifth embodiment. In the same manner as in the fifth embodiment, the tubular member 70F is disposed to cover the coil body 40D, as well as the first intermediate small-diameter portion 15m and a part on the distal end side of the second intermediate small-diameter portion 31m, each exposed from the coil body 40D. The distal end side of the tubular member 70F is fixed to the first intermediate small-diameter portion 15m of the first core shaft 10D by caulking a distal end portion 70d. The proximal end side of the tubular member 70F is fixed to the second intermediate small-diameter portion 31m of the second core shaft 30D by caulking the proximal end portion 70p. In the example of the figure, the inside of the tubular member 70F is a void without the joining agent, and the tubular member 70F is not fixed to the coil body 40D. A length L71 of the tubular member 70F in the axis line O direction after the caulking is larger than a length L72 of the coil body 40D in the axis line O direction. The lengths L71 and L72 can be arbitrarily determined.

In this way, as the method for fixing the tubular member 70F to the first and second core shafts 10D and 30D, various methods (e.g. caulking, welding, or the like) other than application of the joining agent can be adopted. In addition, the tubular member 70F only needs to be fixed to the first and second core shafts 10D and 30D, and is not necessarily fixed to the coil body 40D. Incidentally, in the configuration according to the seventh embodiment, for example, the joining agent may be further applied to the inside of the tubular member 70F. In addition, inside the tubular member 70F, the coil body 40D may be fixed to the first and second core shafts 10D and 30D by the inner fixation portion 90 (FIG. 9). The same effect as in the first embodiment can also be exhibited by the guide wire 1F according to the seventh embodiment.

Eighth Embodiment

Figure 11:
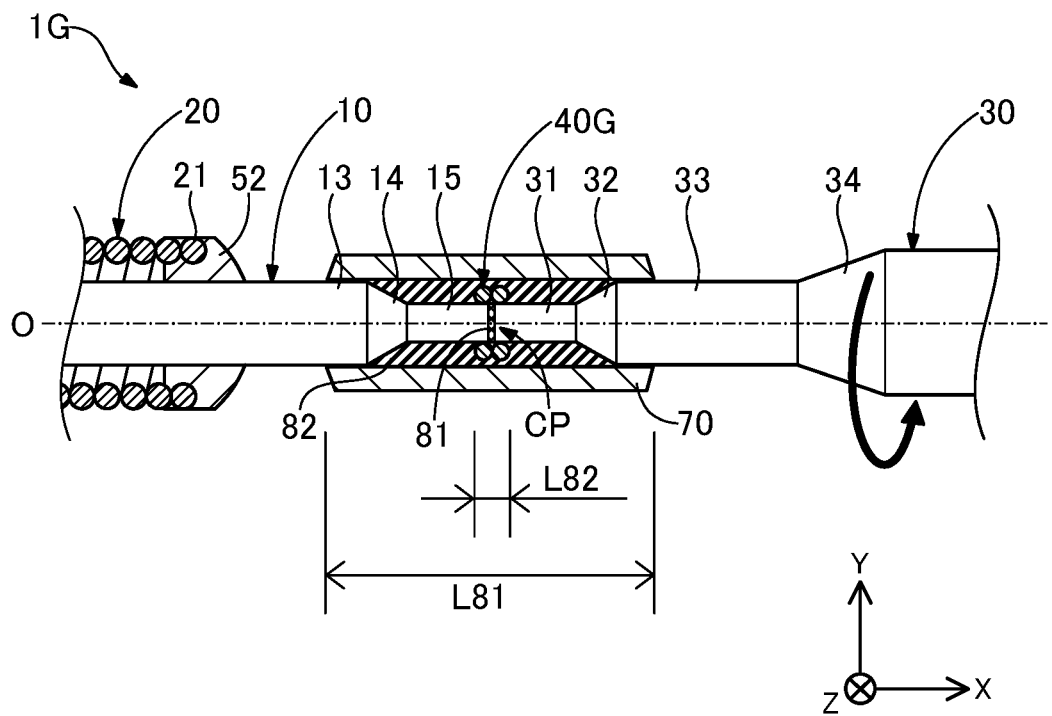
FIG. 11 is a partial sectional view illustrating a vicinity of a contact portion between first and second core shafts of a guide wire according to the eighth embodiment.

FIG. 11 is a partial sectional view illustrating a vicinity of a contact portion between first and second core shafts 10 and 30 of a guide wire 1G according to the eighth embodiment. The guide wire 1G according to the eighth embodiment includes a coil body 40G in which a length L82 in the axis line O direction is short in the configuration according to the first embodiment. The coil body 40G is disposed so as to cover the contact portion CP between the first and second core shafts 10 and 30, a part of the first core shaft 10 adjacent to the contact portion CP (in the example of the figure, a part on the proximal end side of the first small-diameter portion 15), and a part of the second core shaft 30 adjacent to the contact portion CP (in the example of the figure, a part on the distal end side of the second small-diameter portion 31). Also, in the present embodiment, a length L81 of the tubular member 70 in the axis line O direction is larger than the length L82 of the coil body 40G in the axis line O direction. The lengths L81 and L82 can be arbitrarily determined.

In this way, as long as the coil body 40G covers the contact portion CP and a part of each of the first and second core shafts 10 and 30 adjacent to the contact portion CP, the coil body 40G can have any length, and does not necessarily cover the whole of the first and second small-diameter portions 15 and 31. The same effect as in the first embodiment can also be exhibited by the guide wire 1G according to the eighth embodiment.

Ninth Embodiment

Figure 12:
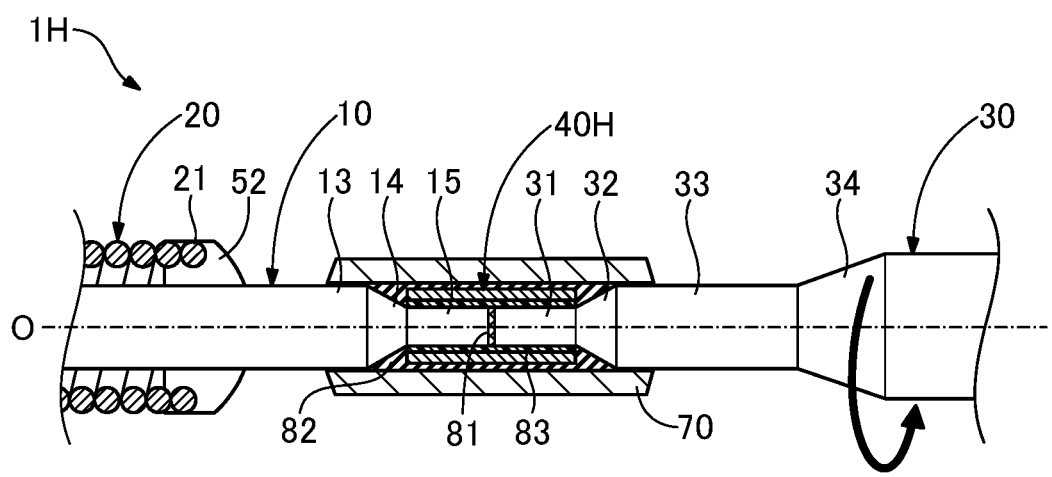
FIG. 12 is a partial sectional view illustrating a vicinity of a contact portion between first and second core shafts of a guide wire according to the ninth embodiment.

FIG. 12 is a partial sectional view illustrating a vicinity of a contact portion between first and second core shafts 10 and 30 of a guide wire 1H according to the ninth embodiment. The guide wire 1H according to the ninth embodiment includes a tubular body 40H made of a resin or a metal instead of the coil body 40 in the configuration according to the first embodiment. The tubular body 40H is made of a material having a lower rigidity than the rigidities of each of the first core shaft 10, the second core shaft 30, and the tubular member 70. The rigidity of the tubular body 40H does not necessarily result from the material itself constituting the tubular body 40H, and the rigidity may be adjusted by the shape of the tubular body 40H. In addition, the tubular body 40H is fixed to the first and second core shafts 10 and 30 by a joining agent 83 applied inside the tubular body 40H. For the joining agent 83, any joining agent can be used similarly to the joining agent 81. For the joining agent 83 and the joining agent 81, the same joining agent or different joining agents can be used.

In this way, the same effect as in the first embodiment can also be exhibited by the guide wire 1H according to the ninth embodiment by covering the contact portion CP of the first and second core shafts 10 and 30 by the tubular body 40H with the adjusted rigidity.

MODIFICATION EXAMPLES OF THE EMBODIMENTS

Note that the disclosed embodiments are not limited to the above embodiments, and can be implemented in various aspects without departing from the gist of the disclosed embodiments. For example, the following modifications are also possible.

Modification Example 1

In the aforementioned first to ninth embodiments, the configurations of the guide wires 1 and 1A to 1H have been described as examples. However, the configuration of the guide wire can be variously modified. For example, the guide wire according to each embodiment has been explained as a medical appliance used for inserting a catheter into a blood vessel, but can be configured as a guide wire to be inserted into each organ in a human body, such as a lymphatic system, a biliary system, a urinary system, a respiratory system, a digestive system, a secretory gland, and a genital organ. For example, the guide wire may be configured such that the whole of the first and second core shafts (in other words, throughout from the distal end portion of the first core shaft to the proximal end portion of the second core shaft) is covered by the coil body. For example, the guide wire may be productized in a state that the distal end side is previously curved.

Modification Example 2

In the first to ninth embodiments, the configurations of the first and second core shafts 10, 10A, 10B, 10D, 30, 30A, 30B, 30D have been described as examples. However, the configurations of the first core shaft and the second core shaft can be variously modified. For example, the first core shaft does not necessarily include the distal small-diameter portion or the distal decreasing-diameter portion, and the second core shaft does not necessarily include the proximal decreasing-diameter portion or the proximal large-diameter portion. For example, the first core shaft may be made of various materials other than the superelastic material, and the second core shaft may be made of a material having a higher rigidity than that of the first core shaft. The first and second core shafts may be formed of the same material. For example, the transverse sectional shape of each portion in the first and second core shafts is not necessarily a substantially circular shape, and various shapes (e.g. a substantially rectangular shape, a substantially elliptical shape, and the like) can be adopted.

Modification Example 3

In the first to ninth embodiments, the configuration of the coil body 20 has been described as an example. However, the configuration of the coil body can be variously modified. For example, the coil body may have a densely-wound structure without gaps between the wires adjacent to each other, or a coarsely-wound (loosely-wound) structure with gaps between the wires adjacent to each other, or a mixed structure of the densely-wound structure and the coarsely-wound structure. In addition, the coil body may have a resin layer coated with e.g. a hydrophobic resin material, a hydrophilic resin material, or a mixture thereof. For example, a transverse sectional shape of the wire of the coil body is not necessarily the substantially circular shape.

Modification Example 4

In the first to ninth embodiments, the configurations of the coil bodies 40, 40B, 40D, 40G, and the tubular body 40H as the first tubular member have been described as examples. However, the configuration of the first tubular member can be variously modified. For example, the first tubular member may be not the multi-thread coil but a single coil formed by spirally winding one wire. In addition, the first tubular member may include a base layer, for example, for the joining agent. For example, the transverse sectional shape of the wire constituting the first tubular member is not necessarily the substantially circular shape. For example, the first tubular member may be configured to have a bending rigidity that is substantially equivalent to or higher than that of the second core shaft.

Modification Example 5

In the first to ninth embodiments, the configurations of the tubular members 70, 70C, 70D, 70F as the second tubular member have been described as examples. However, the configuration of the tubular member can be variously modified. For example, the tubular member may be made of a material other than metal (e.g. resin or the like). For example, through-holes that are filled with the joining agent may be formed on the tubular member. For example, the tubular member may be configured to have a bending rigidity that is substantially equivalent to or higher than that of the second core shaft, and to have an elastic modulus different from that of the first core shaft.

Modification Example 6

The configurations of the guide wires 1 and 1A to 1H according to the first to ninth embodiments, and the configurations of the guide wires according to the modification examples 1 to 5 may be appropriately combined. For example, in the guide wire 1A according to the second embodiment (configuration without the first and second intermediate portions), the guide wire 1B according to the third embodiment (configuration without the first and second small-diameter portions), and the guide wires 1D to 1F according to the fifth to seventh embodiments (configuration having the first and second intermediate small-diameter portions and the first and second end portion-side small-diameter portions), the tubular member 70C having a length explained in the fourth embodiment may be used, and the coil body 40G having a length explained in the eighth embodiment may be used. For example, in the guide wires 1D to 1F according to the fifth to seventh embodiments (configuration having the first and second intermediate small-diameter portions, and the first and second end portion-side small-diameter portions), the tubular member 70 covering parts of the first and second large-diameter portions explained in the first embodiment may be used.

As described above, the present aspects have been explained based on the embodiments and the modification examples, and the embodiments of the aforementioned aspects are intended to facilitate understanding of the present aspects and not to limit the present aspects. The present aspects can be modified and improved without departing from the gist of the aspects and claims, and the present aspects include equivalents thereof. In addition, if technical characteristics of the present aspects are not explained as essential in this specification, the technical characteristics can be appropriately deleted.

DESCRIPTION OF REFERENCE NUMERALS 1, 1A to 1H Guide wire
10, 10A, 10B, 10D First core shaft
11 Distal small-diameter portion
12 Distal decreasing-diameter portion
13 First large-diameter portion
14 First intermediate portion
15 First small-diameter portion
15$e$ First end portion-side small-diameter portion
15$m$ First intermediate small-diameter portion
20 Coil body
21 Wire
30, 30A, 30B, 30D Second core shaft
31 Second small-diameter portion
31$e$ Second end portion-side small-diameter portion
31$m$ Second intermediate small-diameter portion
32 Second intermediate portion
33 Second large-diameter portion
34 Proximal decreasing-diameter portion
35 Proximal large-diameter portion
40, 40B, 40D, 40G Coil body
40H Tubular body
41 Wire
51 Distal end-side fixation portion
52 Proximal end-side fixation portion
61 Intermediate fixation portion
70, 70C, 70D, 70F Tubular member
81 Joining agent
82, 82C Joining agent
83 Joining agent
90 Inner fixation portion

What is claimed is:
1. A guide wire comprising:
a first core shaft;
a second core shaft positioned on a proximal end side of the first core shaft so that a longitudinal axis of the first core shaft coincides with a longitudinal axis of the second core shaft;
a first tubular member covering (i) a contact portion between the first core shaft and the second core shaft where the first core shaft and the second core shaft face each other, (ii) a part of the first core shaft that is adjacent to the contact portion, and (iii) a part of the second core shaft that is adjacent to the contact portion;

a second tubular member covering the first tubular member and fixed to both the first core shaft and the second core shaft; and a coil body covering a portion of a distal end side of the first core shaft, wherein the second tubular member is located away from a proximal end of the coil body toward the proximal end, and wherein the first core shaft includes a portion that is not covered by either the coil body or the second tubular member between the coil body and the second tubular member.

2. The guide wire according to claim 1, wherein:

a length of the second tubular member in an axial direction is larger than a length of the first tubular member in the axial direction; and the second tubular member covers at least a part of the first core shaft that is exposed from the first tubular member, and at least a part of the second core shaft that is exposed from the first tubular member.

3. The guide wire according to claim 1, wherein the second tubular member is fixed to the first core shaft, the second core shaft, and the first tubular member by a joining agent inside the second tubular member.

4. The guide wire according to claim 1, wherein:

the first core shaft comprises:
  a first large-diameter portion; and
  a first small-diameter portion having a diameter that is smaller than a diameter of the first large-diameter portion, the second core shaft comprises:
  a second large-diameter portion; and
  a second small-diameter portion having a diameter that is smaller than a diameter of the second large-diameter portion, the contact portion includes an end portion of the first small-diameter portion and an end portion of the second small-diameter portion that face each other, the first tubular member covers the contact portion and at least a part of the first small-diameter portion that is adjacent to the contact portion and at least a part of the second small-diameter portion that is adjacent to the contact portion, and the second tubular member covers the first tubular member and at least a part of the first large-diameter portion that is exposed from the first tubular member and at least a part of the second large-diameter portion that is exposed from the first tubular member.

5. The guide wire according to claim 1, wherein:

the first tubular member is a multi-thread coil comprising a plurality of wires, and the second tubular member is made of a superelastic material.

6. The guide wire according to claim 1, wherein:

the first core shaft is made of a superelastic material, and the second core shaft is made of a material having a rigidity higher than a rigidity of the superelastic material.

7. The guide wire according to claim 1, wherein a rigidity of the first tubular member is less than each of a rigidity of the first core shaft, a rigidity of the second core shaft, and a rigidity of the second tubular member.

8. The guide wire according to claim 7, wherein the first tubular member is made of a resin.

9. The guide wire according to claim 2, wherein the second tubular member is fixed to the first core shaft, the second core shaft, and the first tubular member by a joining agent inside the second tubular member.

10. The guide wire according to claim 2, wherein:

the first core shaft comprises:
  a first large-diameter portion; and
  a first small-diameter portion having a diameter smaller than a diameter of the first large-diameter portion, the second core shaft comprises:
  a second large-diameter portion; and
  a second small-diameter portion having a diameter smaller than a diameter of the second large-diameter portion, the contact portion includes an end portion of the first small-diameter portion and an end portion of the second small-diameter portion that face each other, the first tubular member covers the contact portion and at least a part of the first small-diameter portion that is adjacent to the contact portion and at least a part of the second small-diameter portion that is adjacent to the contact portion, and the second tubular member covers the first tubular member and at least a part of the first large-diameter portion that is exposed from the first tubular member and at least a part of the second large-diameter portion that is exposed from the first tubular member.

11. The guide wire according to claim 2, wherein:

the first tubular member is a multi-thread coil comprising a plurality of wires, and the second tubular member is made of a superelastic material.

12. The guide wire according to claim 2, wherein:

the first core shaft is made of a superelastic material, and the second core shaft is made of a material having a rigidity higher than a rigidity of the superelastic material.

13. The guide wire according to claim 2, wherein a rigidity of the first tubular member is less than each of a rigidity of the first core shaft, a rigidity the second core shaft, and a rigidity the second tubular member.

14. The guide wire according to claim 13, wherein the first tubular member is made of a resin.

15. The guide wire according to claim 3, wherein:

the first core shaft comprises:
  a first large-diameter portion; and
  a first small-diameter portion having a diameter smaller than a diameter of the first large-diameter portion, the second core shaft comprises:
  a second large-diameter portion; and
  a second small-diameter portion having a diameter smaller than a diameter of the second large-diameter portion, the contact portion includes an end portion of the first small-diameter portion and an end portion of the second small-diameter portion that face each other, the first tubular member covers the contact portion and at least a part of the first small-diameter portion that is adjacent to the contact portion and at least a part of the second small-diameter portion that is adjacent to the contact portion, and the second tubular member covers the first tubular member and at least a part of the first large-diameter portion that is exposed from the first tubular member and at least a part of the second large-diameter portion that is exposed from the first tubular member.

16. The guide wire according to claim 3, wherein:

the first tubular member is a multi-thread coil comprising a plurality of wires, and the second tubular member is made of a superelastic material.

17. The guide wire according to claim 3, wherein:
the first core shaft is made of a superelastic material, and
the second core shaft is made of a material having a rigidity higher than a rigidity of the superelastic material.

18. The guide wire according to claim 3, wherein a rigidity of the first tubular member is less than each of a rigidity of the first core shaft, a rigidity of the second core shaft, and a rigidity of the second tubular member.

19. The guide wire according to claim 18, wherein the first tubular member is made of a resin.

20. The guide wire according to claim 4, wherein:
the first tubular member is a multi-thread coil comprising a plurality of wires, and
the second tubular member is made of a superelastic material.

* * * * *